(12) United States Patent
Bogdanovic et al.

(10) Patent No.: US 6,225,504 B1
(45) Date of Patent: May 1, 2001

(54) PHOSPHANES, THEIR METHOD OF PRODUCTION AND USE IN METAL COMPLEXES

(75) Inventors: Sandra Bogdanovic, Frankfurt; Matthias Beller, Ismaning; Alexander Zapf, Roscnheim; Jurgen Krauter, Augsburg, all of (DE)

(73) Assignee: Celanese GmbH (DE)

( * ) Notice: Subject to any disclaimer, the term of this patent is extended or adjusted under 35 U.S.C. 154(b) by 0 days.

(21) Appl. No.: 09/331,826

(22) PCT Filed: Dec. 11, 1997

(86) PCT No.: PCT/EP97/06931

§ 371 Date: Jun. 23, 1999

§ 102(e) Date: Jun. 23, 1999

(87) PCT Pub. No.: WO98/28315

PCT Pub. Date: Jul. 2, 1998

(30) Foreign Application Priority Data

Dec. 23, 1996 (DE) ................................. 196 54 180

(51) Int. Cl.$^7$ ...................................... C07F 9/50
(52) U.S. Cl. .................. 568/8; 568/16; 568/17; 536/4.1; 536/18.5; 536/55.3
(58) Field of Search ..................... 536/4.1, 18.5, 536/55.3; 568/8, 16, 17

(56) References Cited

PUBLICATIONS

O. Neunhoffer et al., Diphenyl–(p–hydroxy–phenyl) . . ., Chemische Berichte,vol. 94, No. 9, 1961.*

Dess et al, "Phase–Transfer . . . Galactopyranosides", Synthesis, No. 11, Nov. 1981, Stuttgart, DE, pp. 883–885.

Roy et al, "Carbohydrate . . . Transfer Catalysis", Canadian Journal of Chemistry, vol. 69, No. 5, May 1991, pp. 817–821.

Beller et al, "Carbohydrate . . . Catalysis", Angewandte Chemie, International Edition, vol. 36, No. 7, Apr. 18, 1997, pp. 772–774.

* cited by examiner

Primary Examiner—James O. Wilson
Assistant Examiner—Howard Owens
(74) Attorney, Agent, or Firm—Bierman, Muserlian and Lucas

(57) ABSTRACT

A process for the preparation of the formula $$Ar^1{}_{3-x}P[(Ar^2(OZ)_y]_x \qquad I$$

wherein $Ar^1$ and $Ar^2$ are individually aromatic of 6 to 20 carbon atoms or heteroaromatic of 4 to 9 carbon atoms, each unsubstituted or substituted with at least one member of the group consisting of halogen, carboxyl, —OH, alkyl of 1 to 6 carbon atoms, phenyl and naphthyl, $Ar^1$ has one valence and $R^2$ has y+1 valences, x is an integer of 1, 2 or 3, y is 1 or 2, Z is carbohydrate with a glycosidic bond comprising reacting a hydrocarbon halide of the formula $$Z'—X \qquad II$$

when Z' has the definition of Z with —OH protected and X is chlorine, bromine or fluorine with a phosphane of the formula $$Ar^1{}_{3-x}P[(Ar^2(OH)_y]_x \qquad III$$

in a multi-phase reaction medium in the presence of a base and a phase transfer catalyst to form a phosphane of the formula $$Ar^1{}_{3-x}P[(Ar^2(OZ^1)_y]_x \qquad IV$$

and removal of the protective groups to form a compound of Formula I, metal complexes thereof and various processes.

13 Claims, No Drawings

PHOSPHANES, THEIR METHOD OF PRODUCTION AND USE IN METAL COMPLEXES

FIELD OF THE INVENTION

The invention relates to hydrophilic phosphanes, a process for their production, their use in metal complexes, these metal complexes and their use in catalytic conversions.

STATE OF THE ART

Many chemical conversions of organic compounds are carried out under conditions of homogeneous catalysis. A general problem of homogeneous catalysis is the simple and economical separation, following the conversion, of the catalyst system from the organic products. The catalysts should advantageously be simple to separate from the organic products and be recyclable into the conversion process. A solution to these problems represents the so-called two-phase catalysis in which the catalyst system and the organic products are present in different phases and can be separated one from the other by simple decanting. Such two phase-catalyzed conversions are described for example in W. A. Herrmann, C. W. Kohlpaintner, Angew. Chem. 1993, 105, 1588–1609 and in P. Kalck, F. Monteil, Adv. Organomet. Chem. 1992, 34, 219. In these conversions a hydrophilic aqueous phase is frequently used as the catalyst phase, however, it is also possible to use fluoridated hydrocarbons or polyethylene glycols. The prerequisite for an effective two-phase catalysis is high solubility of the catalyst system in the catalyst phase and low solubility in the product phase. For this purpose mainly hydrophilically modified ligands have been used in the past when using metal complex catalysts. A typical example of this are sulfonated triaryl phosphanes such as are described for example in W. A. Herrmann, C. W. Kohlpaintner, Angew. Chem. 1993, 105, 1588–1609 and in P. Kalck, F. Monteil, Adv. Organomet. Chem. 1992, 34, 219. They are used commercially for the hydroformylation of propene. Up to now ionic groups such as $-SO_3^-$, $-CO_2^-$, $-NR_3^+$, $-P(O)O_2^{2-}$ have substantially been used to increase the hydrophilicity of phosphane ligands. This is described for example in M. Beller, B. Cornils, C. D. Frohning, C. W. Kohlpaintner, J. Mol. Catal. 1995, 104, 17–85. Ionic functionalities can be of disadvantage in various processes due to the salt concentrations present. Furthermore, no chiral ionic groups are accessible. To avoid these disadvantages, neutral substituents can be used. As neutral substituents in order to increase the hydrophilicity of phosphanes have previously been used for example polyethylene glycol groups. This is described for example in B. Cornils, Angew. Chem. 1995, 107, 1709–1711.

OBJECTS OF THE INVENTION

The task of the present invention is providing hydrophilic phosphane compounds which can be used as metal complex ligands for the production of catalysts and which make accessible a multiplicity of structural variants including chiral centers.

SUMMARY OF THE INVENTION

This task is solved through a process for the production of phosphanes having the general formula (I)

$$Ar^1_{3-x}P(Ar^2(OZ)_y)_x \qquad (I)$$

in which $Ar^1$ and $Ar^2$ independently are aromatic $C_{6-20}$ radicals or heteroaromatic $C_{4-9}$ radicals substituted, if appropriate, by halogen atoms, carboxyl groups, hydroxyl groups, $C_{1-6}$ alkyl groups, phenyl groups or naphthyl groups wherein $Ar^1$ has one and $Ar^2$ has y+1 free valences, Z is a carbohydrate radical with a glycosidic bond, x has the value 1, 2 or 3, and y has the value 1 or 2, by (1) the conversion of carbohydrate halogenoses having the general formula (II)

$$Z'-X \qquad (II)$$

in which Z' is a radical Z as specified above, in which the hydroxyl groups are substituted by protective groups, and X represents Br, Cl or F, with a phosphane having the general formula (III)

$$Ar^1_{3-x}P(Ar^2(OH)_y)_x \qquad (III)$$

in which $Ar^1$, $Ar^2$, x and y have the above meaning in a multiphase reaction medium in the presence of a base and of a phase transfer catalyst, into a phosphane having the general formula (IV)

$$Ar^1_{3-x}P(Ar^2(OZ')_y)_x \qquad (IV)$$

in which $Ar^1$, $Ar^2$, x, y and Z' have the above specified meaning, and (2) removal of the protective groups from Z'.

It was found according to the invention that the compounds having the general formulas (I) and (IV) are accessible through the phase transfer-catalyzed conversion of carbohydrate halogenoses.

Only O. Neunhoeffer, L. Lamza, Chem. Ber. 1961, 94, 2514–2521 have published the synthesis of a triphenyl phosphane in which one phenyl radical in the p-position is substituted by a glucosyl radical, in which the hydroxyl groups are protected by acetyl groups. The production takes place through the glycosylation in aqueous acetone with potassium hydroxide as a base. The yield was 8% and was thus substantially less than the yields obtainable in the process according to the invention.

The phosphanes produced according to the invention have the general formula (I)

$$Ar^1_{3-x}P(Ar^2(OZ)_y)_x \qquad (I)$$

In the formula (I) the radicals $Ar^1$ and $Ar^2$ are aromatic $C_{6-20}$ radicals or heteroaromatic $C_{4-9}$ radicals. As aromatic radicals they are therein preferably independently phenyl, naphthyl, biphenyl or binaphthyl radicals. If several $Ar^1$ or $Ar^2$ radicals are present, each individual radical can independently be one of the above radicals. At least one aromatic radical $Ar^1$ or $Ar^2$ is therein preferably a phenyl radical and, especially preferred, two of the aromatic radicals are phenyl radicals. In particular all of the aromatic radicals $Ar^1$ and $Ar^2$ are phenyl radicals.

The radicals $Ar^1$ and/or $Ar^2$ as the heteroaromatic radicals comprise preferably 1 or 2, especially preferably 1 hetero atom selected from oxygen, sulphur and nitrogen. Especially preferred are radicals based on pyridine, furan or thiophene. The aromatic radicals can, if appropriate, be substituted independently of one another, for example by halogen atoms, carboxyl groups, hydroxyl groups, $C_{1-6}$, preferably $C_{1-2}$ alkyl groups, phenyl groups or naphthyl groups. These substituents can be present in addition to the substituent(s) OZ of the radical $Ar^2$. The substituents are preferably hydroxyl groups, in particular maximally one hydroxyl group per benzene nucleus is present.

Ar[1] comprises one and Ar[2] comprises y+1 free valences. y has therein the value 1 or 2. If the radical Ar[2] is a radical based on a phenyl radical, at y=1 the free valences can be present in the o-, m- or p-position. The free valences are preferably present in the o- or p-, in particular in the p-position. In the case of biphenyl radicals or binaphthyl radicals as the radicals Ar[2], the valences are preferably present in different benzene nuclei i.e. each phenyl or naphthyl radical preferably contains at least one of the free valences. y has preferably the value 1.

x can have the value 1, 2 or 3. x preferably has the value 1 or 2, in particular the value 1. y has preferably the value 1.

Preferred compounds of formula (I) are such in which y=1 and x=1 or 2. The radical Ar[1] is therein preferably a phenyl radical or a phenyl radical substituted by an hydroxyl in the p-position. The radical Ar[2] is preferably a p-phenylene radical or a binaphthyl radical, in particular a 1,1'-binaphthyl radical in which the free valences are in the 2,2'-position.

The radical Z is a carbohydrate radical with a glycosidic bond which is derived from a sugar radical. Z is preferably derived from glucose, mannose, galactose, fructose, cellobiose, saccharose, glucosamine, N-acetylglucosamine or their stereoisomers. Consequently, Z is preferably derived from a glycosidically linked 5 or 6-member carbohydrate. Corresponding amines or N-acetylamines of these compounds can also be used. Each radical Z independently has one of the above meanings.

Z is preferably derived from glucose, galactose or N-acetylglucosamine.

The phosphanes according to the invention having the general formula (I) are produced by the conversion of carbohydrate halogenoses having the general formula (II)

$$Z'\text{---}X \qquad (II)$$

Z' is therein a radical Z as was described above, with the difference that the hydroxyl groups are substituted by protective groups. Suitable protective groups which protect the hydroxyl groups during the conversion against reacting are known to a person skilled in the art. Examples are acetyl, benzoyl, benzyl or allyl groups. The protective groups are distinguished thereby that they prevent in particular a reaction of the protected hydroxyl groups in glycosylation reactions. Acetyl protective groups are preferably used. The production of the compounds Z'—X can take place for example according to the process described in R. R. Schmidt, Angew. Chem. 1986, 98, 213–236. The corresponding monosacharide is therein converted for example with a base and an acylation agent and, if appropriate, an acylation catalyst. The resulting peracylated compound is converted into glacial acetic acid with an HX acid, preferably hydrobromic acid. Following standard processing methods, the protected halogenose is obtained. The compounds having the formula Z'—X in which X is bromine, chlorine, fluorine, in particular bromine or chlorine, are converted with a phosphane having the general formula (III)

$$Ar^{1}{}_{3-x}P(Ar^{2}(OH)_{y})_{x} \qquad (III)$$

Ar[1], Ar[2], x, y have therein the above specified meaning. The conversion takes place in a multiphase, in particular two-phase, reaction medium in the presence of a base and of a phase transfer catalyst. The reaction takes place at conversion temperatures of 0 to 80° C., preferably 10 to 60° C., in particular 20 to 50° C. As the reaction media can be used all suitable two- or multiphase reaction media. One phase of the reaction medium is preferably an aqueous phase, and in this phase water can be present in a mixture with a water-soluble organic solvent. The second phase is an organic phase which is only slightly or not at all mixable with water. Examples of suitable two-phase reaction media are dichloromethane/water, acetone/water, toluene/water, toluene/ethylene glycol, tert. butyl methylether/water or dichloromethane/polyethylene glycol.

Suitable bases are alkali and alkaline earth hydroxides, basic amines and salts of weak acids. Basic amines are for example pyridine, tributylamine, benzylamine, triethylamine, diisopropylethylamine. Salts of weak acids are for example sodium acetate, potassium benzoate, sodium carbonate, sodium hydrogenphosphate. Alkali and alkaline earth hydroxides, such as NaOH, KOH, LiOH, Ca(OH)$_2$, Mg(OH)$_2$ are preferably used, with NaOH and KOH being especially preferred.

Catalysts suitable as phase transfer catalysts are for example described in Eckehard N. Dehmlow, Sigrid S. Dehmlow, Phase Transfer Catalysis, 3rd Edition, VCH, Weinheim, New York, Basel, Cambridge, Tokio (1993). Tetra-n-C$_{1-12}$ alkylammonium salts are preferably used. Especially preferred is therein the use of tetra-n-butyl ammonium salts. As counterions can be used all suitable inorganic counterions, for example halogenides or hydrogen sulfates. Especially preferred examples are tetra-n-butyl ammonium bromide, tetra-n-butyl ammonium hydrogen sulfate, tetra-n-butyl ammonium chloride, tetra-n-butyl ammonium nitrate. The phase transfer catalysts are preferably used in quantities from 1 to 90 percent by weight relative to halogenose.

To prepare N-acetylglucosamine compounds the following steps are preferably carried out:

Suitable N-acetylglucosamine donors are described for example in T. Mukaiyama et al., Chem. Lett. 1984, 907; K. Higashai, Chem. Pharm. Bull. 1990. 38, 3280. Of the various glucosamine donors the glucopyranosyl chloride is accessible directly in one stage by conversion with acetyl chloride. This is described for example in D. Horton, Org. Synth., Coll. Vol. V, 1973, 1. Furthermore, the process described in G. Chittenden, Carbohydr. Res. 1993, 242, 297 can be followed. As phase transfer catalyst for the coupling reaction is preferably used zinc chloride which yields good alpha/beta selectivity (T. Norberg, J. Carbohydr. Chem. 1990, 9, 721). The conversion takes preferably place in the presence of co-catalysts. Suitable co-catalysts are described for example in R. Bittman, Tetrahedron Lett., 1994, 35, 505. Instead of the trityl chloride used in this paper, a 4,4'-dimethoxytrityl halogenide is used in combination with zinc fluoride. This permitted preventing epimerization, moreover, the conversion occurs more readily. When using this catalyst combination a marked shortening of the reaction time could be attained even with relatively large reaction mixtures. Thus for the preparation of N-acetylglucosamine derivatives the catalyst combination zinc chloride/4,4'-dimethoxy trityl halogenide is preferably used as phase transfer catalyst. Moreover, when using this catalyst system the chromatographic purification of the products is simplified. The shorter reaction time permits the specific synthesis of beta-glycosidically linked N-acetyl glucosamine derivatives with good yields and without epimerization occurring.

After the conversion into phosphanes having the general formula (IV), the protective groups are removed from Z'. Suitable processes are described for example in R. R. Schmidt, Angew. Chem. 1986, 98, 213–236. The splitting of acetyl protective groups takes preferably place under basic conditions.

The process according to the invention makes possible the production of a multiplicity of carbohydrate-substituted triphenyl phosphanes in short reaction times and with high yield.

The invention also relates to phosphanes having the general formula (I), such as are defined above. The invention furthermore relates to phosphanes having the general formula (IV) such as are defined above. The exception are compounds in which $Ar^1$ =phenyl, $Ar^2$ =p-phenylene, Z'=acetyl-protected glucosyl radical, x=1, y=1.

Examples of preferred compounds having the general formula (IV) are the following: diphenyl-(o-hydroxyphenyl)-phosphine-2,3,4,6-tetra-O-acetyl-,β-D-glucopyranoside, 1-O-[4-(diphenylphosphino)phenyl]-2-acetamido-2-desoxy-3,4,6-O-acetyl-β-D-glucopyranoside.

Preferred phosphanes having the general formula (I) correspond to these compounds with the protective groups having been removed.

The phosphanes according to the invention having the general formula (I) can be used for the production of metal complexes. As the central metal atom the following metals can be used therein: Ru, Pd, Rh, Ni, Pt, Co, Ir, Cu, Fe, Mn. In addition to the phosphanes according to the invention having the general formula (I), the metal complexes can comprise as ligands further ligands, such as halogen atoms, hydrogen atoms, carbon monoxide, etc.

The invention also relates to ruthenium complexes having the general formula (V)

$$RuH_2(CO)L_3 \quad (V)$$

in which L is a phosphane having the general formula (I) such as is described above. The complexes are produced by converting the phosphane with ruthenium(III) chloride trihydrate according to the process described in J. J. Levison, S. D. Robinson, J. Chem. Soc. A 1970, 2947–2954.

The invention also relates to palladium complexes having the general formula (VI)

$$L_2PdX_2 \quad (VI)$$

in which L is a phosphane having the general formula (I) as described above and X is Cl, Br, I, preferably Cl, or acetate. The production takes place for example with lithium tetrachloropalladate(II) in ethanol according to the process described in G. Brauer, Handbuch der praparativen anorganischen Chemie, Ferdinand Enkel Verlag, 1981, Vol. 3, p. 2014.

The complexes in which X is acetate, can be generated in situ from $Pd(OAc)_2$ and the corresponding ligands in the reaction mixture. The ratio of Pd to ligand is therein preferably 1:1 to 1:20, especially preferred 1:2 to 1:10, in particular approximately 1:3. Under reducing conditions are therefrom formed palladium complexes having the general formula (VII)

$$L_zPd \quad (VII)$$

in which L is a phosphane having the general formula (I) and z has the value 3 or 4.

The catalysts according to the invention can be used in catalytic C—C coupling reactions. Examples of such coupling reactions are the Heck reaction, the Suzuki reaction or hydroformylations, they are furthermore suitable for hydrogenations of unsaturated compounds, hydrogenations of aromatic nitro substances, allyl substitutions, carbonylations and polymerizations.

In the following the invention will be explained in further detail in conjunction with examples.

EXAMPLE 1

1-O-[4-(diphenylphosphino)phenyl]-2-acetamido-2-desoxy-β-D-glucopyranoside (glycosylation)

202 mg (0.726 mmol) (p-hydroxyphenyl)diphenylphospane and 125 mg (0.368 mmol) tetra-n-butylammonium hydrogen sulfate are dissolved in 2 ml methylene chloride and mixed with 2 ml 1 M sodium hydroxide solution. 133 mg (0.364 mmol) 2-acetamido-3,4,6-tri-O-acetyl-2-desoxy-α-D-glucopyranosyl chloride (1) and after 5 minutes an additional 133 mg (0.364 mmol) of 1 are added. After 15 minutes 0.5 ml 1 M sodium hydroxide solution and 267 mg (0.730 mmol) of 1 and lastly, after 70 minutes, 0.5 ml 1 M sodium hydroxide solution and 259 mg (0.708 mmol) of 1 are added. After 1.5 hours the reaction mixture is diluted with 30 ml ethyl acetate. The organic phase is washed twice, each time with 20 ml 1 M sodium hydroxide solution, twice with 20 ml water each time and once with 15 ml saturated sodium chloride solution. The mixture is dried over magnesium sulfate and the solvents are removed by distillation. The residue is taken up in 10 ml absolute methanol and under nitrogen mixed with 0.5 ml of a 1 M methanolic sodium methanolate solution. After agitating the solution at ambient temperature, it is diluted with 10 ml methanol and neutralized with Amberlyst H 15 (strongly acidic cation exchanger). The ion exchanger is separated by filtration and the solvent is removed by distillation. The residue is chromatographed with chloroform/methanol/hexane 6:1:1 (v/v/v) over 55 g silica gel 60. Yield: 238 mg (68% with respect to phosphane).

1-O-[4-(diphenylphosphino)phenyl]-2-acetamido-2-desoxy-β-D-glucopyranoside (Protection removal)

0.33 mmol 1-O-[4-(diphenylphosphino)phenyl]-2-acetamido-2-desoxy-3,4,6-O-acetyl-β-D-glucopyranoside are suspended in 25 ml methanol and a solution of 2 mg sodium in 25 ml methanol is added. After approximately 2 hours of agitation at ambient temperature, a solution is formed. It is neutralized with acidic ion exchanger (Amberlyst H 15), filtered and the residue is concentrated to dryness. The residue is washed with water and recrystallized from ethanol/water. Yield: 0.32 mmol (96%).

EXAMPLE 2

Diphenyl-(p-hydroxyphenyl)-phosphine-2,3,4,6-tetra-O-acetyl-β-D-glucopyranoside

To a solution of diphenyl-(p-hydroxyphenyl)-phosphine (778 mg, 2.80 mmol) in water/acetone (10 ml/6ml) is added potassium hydroxide (0.35 g). While stirring the mixture, a solution of acetobromoglucose (2.63 g, 6.4 mmol) in acetone (15 ml) is added dropwise. The mixture is agitated for 2 days at ambient temperature. After removing the solvent in a rotary evaporator the residue is rinsed several times with water. The remaining residue is recrystallized from ethanol. The glucopyranoside is obained in the form of a slightly yellow solid substance (450 mg, 26.4%).

$R_f$-value (toluene/ethyl acetate 1/1): 0.61; NMR-$^1$H (300 MHz, DMSO): 7.45–7.18 (m 12 H); 7.07–7.01 (m, 2H), 5.62 (d, J=8,0 Hz, 1H); 5.40 (m, J=8.8 Hz, 1H), 5.06 (m, J=9.7 Hz, J=8.2 Hz, 1H); 5.00 (m, J=9.7 Hz, 1H); 4.28–4.04 (m, 3H (4s, each 3H).

Diphenyl-(p-hydroxyphenyl)-phosphine-β-D-glucopyranoside

Diphenyl-(p-hydroxyphenyl)-phosphine-2,3,4,6-tetra-O-acetyl-β-D-glucopyranoside (196 mg, 0.32 mmol) is dissolved in absolute methanol (5 ml) and mixed with 30% sodium methanolate solution (0.5 ml). The solution is agitated for 3 hours at ambient temperature and neutralized with acidic ion exchanger (Dowex 50 W×8). After removal of the solvent, the glucopyranoside is obtained as a slightly yellow solid substance (139 mg, 97%).

$R_f$-value (dichloromethane/methanol 10/1): 0.3.

EXAMPLE 3

Diphenyl-(o-hydroxyphenyl)-phosphine-2,3,4,6-tetra-O-acetyl-β-D-glucopyranoside

To a solution of diphenyl-(o-hydroxyphenyl)-phosphine (4.33 g, 15.6 mmol) in water/acetone (60 ml/35 ml) is added potassium hydroxide (1.91 g). While stirring the mixture a solution of acetobromoglucose (14.25 g) in acetone (15 ml) is added dropwise. The mixture is agitated for 2 days at ambient temperature. After removing the solvent in a rotary evaporator, the residue is rinsed several times with water. The remaining residue is recrystallized from ethanol. The glucopyranoside is obtained as a slightly yellow solid substance (1.84 g, 19.4%)

$R_f$-value (toluene/ethyl acetate 1/1): 0.6; NMR-$^1$H (300 MHz, DMSO): 7.50–7.00 (m 14H); 5.62 (d, J=8.1 Hz 1H); 5.42 (m, 1=8.7 Hz, 1H), 5.10 (m, J=9.7 Hz, J=8.1 Hz, 1H); 5.00 (m, J=9.7 Hz, 1H); 4.28–4.06 (m, 3H); 2.03–1.95 (4s each 3H).

Diphenyl-(o-hydroxyphenyl)-phosphine-β-D-glucopyranoside

Diphenyl-(o-hydroxyphenyl)-phosphine-2,3,4,6-tetra-O-acetyl-β-D-glucopyranoside (450 mg, 0.74 mmol) is dissolved in absolute methanol (5 ml) and mixed with 30% sodium methanolate solution 0.5 ml). The solution is agitated for 3 hours at ambient temperature and neutralized with acidic ion exchanger (Dowex 50 W×8). After removing the solvent the glucopyranoside is obtained in the form of a slightly yellow solid substance (312 mg, 96%).

$R_f$-value (dichloromethane/methanol 10/1): 0.4.

EXAMPLE 4

Preparation of GlcNAc Chloride

To 500 ml acetyl chloride are added over a period of 2 minutes 250 g (1.13 mol) N-acetyl-(D)-glucosamine. The mixture is stirred for 19 hours at ambient temperature. After adding methylene chloride (500 ml) the solution is placed onto a mixture of ice/water (500 ml) and the organic phase is rapidly separated. The organic phase is rapidly washed with saturated sodium hydrogen carbonate solution, dried over magnesium sulfate and filtered. The mixture is concentrated to one half of the volume in a rotary evaporator. While rapidly agitating the mixture, 500 ml diethylether are added. After 12 hours the resulting precipitate is aspirated and dried under reduced pressure. The chloride is obtained in the form of a slightly brown powder (269 g, 62%).

Diphenyl-(o-hydroxyphenyl)-phosphine-N-acetyl-2-amino-2-desoxy-3,4,6-tri-O-acetyl-β-D-glucopyranoside To a suspension of zinc(II) chloride (139 mg, 1.03 mmol) and 4,4'-dimethoxy tritylchloride (122 mg, 1.34 mmol) in dry dichloromethane (15 ml) the chloride (1.3 eq, 497 mg, 1.34 mmol) and diphenyl-(o-hydroxyphenyl)-phosphine (287 mg, 1.34 mmol) are added. The mixture is agitated for 13 hours at ambient temperature (DC control methylene chloride/methanol 50/1). After adding methylene chloride, the mixture is washed with sat. sodium hydrogen carbonate solution. After removing the solvent in a rotary evaporator, the residue is purified by column chromatography (methylene chloride/methanol 100/1–40/1). The yield of the glycoside obtained is 37% (232 mg).

$R_f$-value (dichloromethane/methanol 50/1): 0.4; NMR-$^1$H (300 MHz, DMSO): 7.51–7.01 (m, 14H); 5.60 (d, J=8.2 Hz, 1H); 5.40 (m, J=8.6 Hz, 1H), 5.15 (m, J=9.7 Hz, J=8.2 Hz, 1H); 5.03 (m, J=9.6 Hz, 1H); 4.28–4.02 (m, 3H); 2.17–1.95 (4s each 3H).

Catalytic Conversions

EXAMPLE 5

Suzuki Reaction 4-bromacetophenone or 1-bromo-4-chlorobenzene were converted accoding to the Suzuki reaction with phenylboric acid ($H_5C_6$—$B(OH)_2$ to the correspondingly substituted biphenylenes. In the reaction the bromine atom was substituted by the phenyl radical. A mixture of 15 mmol phenylboric acid, 13.5 mmol 4-bromaceto phenone or 1-bromo-4-chlorobenzene, 40.5 mmol $Na_2CO_3$ 10 $H_2O$, 0.01 mol percent, relative to phenyl boric acid, $Pd(OAc)_2$, and ligand L at a molar ratio Pd:L of 1:3 were heated to a temperature of 60° C. in a solvent mixture comprising 9 ml ethanol, 9 ml water and 18 ml di-n-butyl ether or 12 ml ethanol, 6 ml water and 15 ml toluene while stirring the mixture. The mixture was subsequently heated for 2 hours to a temperature of 78° C. The conversion product was isolated and the yield was determined. As the ligand was used: 1-O-[4-(diphenylphosphino)phenyl]-2-acetamido-2-desoxy-β-D-glucopyranoside (3a). For purposes of comparison the trisodium salt of 3,3',3"-phosphane triylbenzene-sulfonic acid (TPPTS) was used. The results of the conversion are listed in Table 1 for the conversion with 4-bromacetophenone.

TABLE 1

| Experiment | Ligand | Yield [%] | Solvent | TON |
|---|---|---|---|---|
| 1 | 3a | 87 | 1 | 8700 |
| 2 | TPPTS* | 67 | 1 | 6700 |
| 3 | 3b | 90 | 2 | 9000 |
| 4 | TPPTS* | 87 | 2 | 8700 |

*TPPTS = trisodium salt of 3,3',3"-phosphane triylbenzene-sulfonic acid, comparison ligand Solvent 1: 9 ml ethanol, 9 ml water, 18 ml di-n-butyl ether
Solvent 2: 12 ml ethanol, 6 ml water, 15 ml toluene
TON: version number=mol (product)/mol (catalyst)

Results of the conversion with 1-bromo-4-chlorobenzene are listed in Table 2.

TABLE 2

| Experiment | Ligand | Yield [%] | Solvent | TON |
|---|---|---|---|---|
| 5 | 3a | 56 | 1 | 5600 |
| 6 | TPPTS* | 40 | 1 | 4000 |
| 7 | 3b | 71 | 2 | 7100 |
| 8 | TPPTS* | 44 | 2 | 4400 |

The results listed in Table 1 and 2 demonstrate that yields and conversions with catalyst which comprise the ligands according to the invention are significantly higher than when using the comparison ligand TPPTS.

EXAMPLE 5

Heck Reaction

In the Heck reaction, carried out as a two-phase reaction, 4-bromacetophenone or 1-bromo-4-nitrobenzene, respectively, was converted with styrene to form the correspondingly substituted stilbenes. In the process a mixture comprising 15 mmol 4-bromacetophenone or 1-bromo-4-nitrobenzene, 22.5 mmol (1.5 equivalents) styrene, 16.5 mmol (1.1 equivalents) NaOAc 3 $H_2O$, $Pd(OAc)_2$ in the quantities specified in Table 3 and the ligands listed in the Table at a ratio of Pd:L=1:3 in a mixture comprising 10 ml xylene and 10 ml ethylene glycol was allowed to react under agitation at 130° C. for 20 hours. The conversion product was isolated and its yield was determined. The results are summarized in Table 3 and 4 below:

TABLE 3

Heck reaction with 4-bromacetophenone

| Experiment | Ligand | Yield [%] (EZ) | Catalyst mol [%] | TON |
|---|---|---|---|---|
| 9 | 3a | 98 (89:11) | 1 | 98 |
| 10 | 3b | 80 (95:5) | 1 | 80 |
| 11 | TPPTS* | 79 (92:8) | 1 | 79 |

TABLE 4

Heck reaction with 1-bromo-4-nitrobenzene

| Experiment | Ligand | Yield [%] (EZ) | Catalyst mol [%] | TON |
|---|---|---|---|---|
| 12 | 3a | 85 (95:5) | 0.1 | 850 |
| 13 | 3b | 88 (95:5) | 0.1 | 880 |
| 14 | TPPTS* | 78 (94:6) | 1 | 78 |

Reference is made to the explanations regarding Table 1. The catalysts with the lingands according to the invention exhibit high yields and high conversion numbers at a good ratio of E to Z isomers.

What is claimed is:

1. A process for the preparation of the phosphanes of formula $$Ar^1_{3-x}P[Ar^2(OZ)_y]_x \qquad I$$

wherein $Ar^1$ and $Ar^2$ are individually aromatic rings, each having 6 to 20 carbon atoms, or heteroaromatic rings, each having 4 to 9 carbon atoms, each unsubstituted or substituted with at least one member of the group consisting of halogen, carboxyl, —OH, alkyl of 1 to 6 carbon atoms, phenyl and naphthyl, $Ar^1$ has one valence and $R^2$ has y+1 valences, x is an integer of 1, 2 or 3, y is 1 or 2, Z is a residue of a carbohydrate selected from the group consisting of glucose, mannose, galactose, fructose, cellobiose, saccharose, glucosamine, and their stereoisomers, and their N-acetylamine derivatives, said process comprising forming one new glycosidic bond for each substituent bound to the phosphane by reacting a hydrocarbon halide of the formula $$Z'—X \qquad II$$

wherein Z' has the definition of Z with any —OH protected and X is chlorine, bromine or fluorine, with a phosphane of the formula $$Ar^1_{3-x}P[Ar^2(OH)_y]_x \qquad III$$

in a reaction medium, which contains at least two immiscible liquid phases, at 0° to 80° C. in the presence of a base and a phase transfer catalyst to form a phosphane of the formula $$Ar^1_{3-x}P[Ar^2(OZ^1)_y]_x \qquad IV$$

and removing the protective groups to form the compound of Formula 1.

2. A phosphane of the formula $$Ar^1_{3-x}P[Ar^2(OZ)_y]_x \qquad I$$

wherein $Ar^1$ and $Ar^2$ are individually aromatic rings, each having 6 to 20 carbon atoms, or heteroaromatic rings, each having 4 to 9 carbon atoms, each unsubstituted or substituted with at least one member of the group consisting of halogen, carboxyl, —OH, alkyl of 1 to 6 carbon atoms, phenyl and naphthyl, $Ar^1$ has one valence and $R^2$ has y+1 valences, x is an integer of 1, 2 or 3, y is 1 or 2, Z is a carbohydrate, selected from the group consisting of glucose, mannose, galactose, fructose, cellobiose, saccharose, glucosamine, and their stereoisomers, and their N-acetylamine derivatives with the proviso that when x and y are 1, $Ar^1$ is not phenyl, $Ar^2$ is not p-phenylene and Z is not β-glucosyl.

3. The process of claim 1 wherein Z is derived from glucose, galactose, or n-acetyl glucosamine.

4. The process of claim 1 wherein $Ar^1$ and $Ar^2$ are individually selected from the group consisting of phenyl, naphthyl, biphenyl, binaphthyl and pyridyl.

5. The process of claim 1 wherein the —OH protective group is selected from the group consisting of acetyl, benzoyl, benzyl and allyl.

6. The phosphane of Formula IV of claim 1 with the proviso that when x and y are 1, $Ar^1$ is not phenyl, $Ar^2$ is not p-phenylene and $Z^1$ is not acetyl protected glucosyl.

7. A ruthenium complex of the formula $$RuH_2(CO)L_3 \qquad V$$

wherein L is a phosphane of claim 2.

8. A palladium complex of the formula $$L_2PdX_2 \qquad VI$$

wherein L is a phosphane of claim 2 and X is chlorine or bromine or idomine or acetate.

9. A palladium complex of the formula $$L_zPd \qquad VII$$

wherein L is a phosphane of claim 2 and z is 3 or 4.

10. In a hydroformylation of an olefin, the improvement consisting of performing the hydroformylation in the presence of a catalyst selected from the group consisting of a catalyst of claims 7, 8 and 9.

11. In effecting a Heck reaction, the improvement consisting of performing the reaction in the presence of a catalyst selected from the group consisting of catalysts of claims 7, 8 and 9.

12. In effecting a Suzuki reaction, the improvement consisting of performing the reaction in the presence of a catalyst selected from the group consisting of catalysts of claims 7, 8 and 9.

13. In a hydroformylation of an olefin, the improvement consisting of performing the hydroformylation in the presence of a catalyst comprising rhodium and a phosphane of claim 2.

\* \* \* \* \*